United States Patent [19]
Morris et al.

[11] Patent Number: 5,650,596
[45] Date of Patent: Jul. 22, 1997

[54] AUTOMATIC SURGICAL SPONGE COUNTER AND BLOOD LOSS DETERMINATION SYSTEM

[75] Inventors: Sharon L. Morris; Dean E. Morris, both of River Ridge, La.

[73] Assignee: Surgical Resources, L.L.C., Covington, La.

[21] Appl. No.: 286,413

[22] Filed: Aug. 5, 1994

[51] Int. Cl.⁶ .............................. G01G 19/22; A61M 1/00
[52] U.S. Cl. .................................... 177/25.13; 177/25.19; 177/245; 604/317
[58] Field of Search ...................... 177/15, 25.13, 177/25.19, 245, 45, 25.17; 340/572, 573; 604/317, 318, 403, 404, 407

[56] References Cited

U.S. PATENT DOCUMENTS

| | | | |
|---|---|---|---|
| 3,367,431 | 2/1968 | Baker et al. | 177/25.13 |
| 4,193,405 | 3/1980 | Abels | 177/25.17 |
| 4,295,537 | 10/1981 | McAvinn et al. | 177/15 |
| 4,361,231 | 11/1982 | Patience | 206/362 |
| 4,422,548 | 12/1983 | Cheesman et al. | 206/370 |
| 4,498,076 | 2/1985 | Lichtblau | 177/25.17 |
| 4,510,489 | 4/1985 | Anderson, III et al. | 177/25.17 |
| 4,650,464 | 3/1987 | Ruiz et al. | 604/49 |
| 4,658,818 | 4/1987 | Miller, Jr. et al. | 177/25.17 |
| 4,832,198 | 5/1989 | Alikhan | 206/438 |
| 4,887,715 | 12/1989 | Spahn et al. | 206/370 |
| 4,889,230 | 12/1989 | Zachry | 206/362 |
| 4,903,837 | 2/1990 | Duello | 206/440 |
| 4,922,922 | 5/1990 | Pollock et al. | 128/760 |
| 5,009,275 | 4/1991 | Sheehan | 177/25.13 |
| 5,031,642 | 7/1991 | Nosek | 128/906 |
| 5,057,095 | 10/1991 | Fabian | 604/362 |
| 5,103,210 | 4/1992 | Rode et al. | 177/25.17 |
| 5,107,862 | 4/1992 | Fabian et al. | 128/899 |
| 5,186,322 | 2/1993 | Harreld et al. | 206/216 |
| 5,188,126 | 2/1993 | Fabian et al. | 177/25.17 |
| 5,190,059 | 3/1993 | Fabian et al. | 177/25.17 |
| 5,300,120 | 4/1994 | Knapp et al. | 177/25.17 |
| 5,329,944 | 7/1994 | Fabian et al. | 177/25.17 |
| 5,353,011 | 10/1994 | Wheeler et al. | 177/25.17 |
| 5,357,240 | 10/1994 | Sanford et al. | 177/25.17 |
| 5,381,137 | 1/1995 | Ghaem et al. | 340/572 |

OTHER PUBLICATIONS

Vollrath Brochure on Sponge Track Self-Contained Sponge Counting System. No date given.
PyMaH Corp. Brochure on Keep-a-Count Contain-Count Sponge System (1989).
Indala Corp. Brochure on RF Tags (1993).

*Primary Examiner*—Michael L. Gellner
*Assistant Examiner*—Randy W. Gibson
*Attorney, Agent, or Firm*—Pravel, Hewitt, Kimball & Krieger

[57] ABSTRACT

A device for automatically counting, weighing, and calculating blood loss contained within, soiled surgical sponges includes a cabinet with an opening at the top through which sponges are deposited, a reader which scans each sponge entered and determines sponge type from a tag affixed to each sponge, and a disposable bag into which the sponges are deposited. The disposable bag is removably mounted to a weighing scale; there is also a rear door from which the disposable bag can be easily removed, a rechargeable battery, a shelf for unused disposable bag storage, a control unit which processes data received from reader and scale and instantaneously calculates total weight of liquid contained within sponges entered, a display panel which continuously displays the number and type of sponges entered during a given procedure as well as the total weight of liquids retained in those sponges. There is a means for automatically determining the weight of the sponges when dry which includes a non-optical scanner means which can read an indicating means on the sponges even when the indicating means is covered with blood or other body fluids.

13 Claims, 3 Drawing Sheets

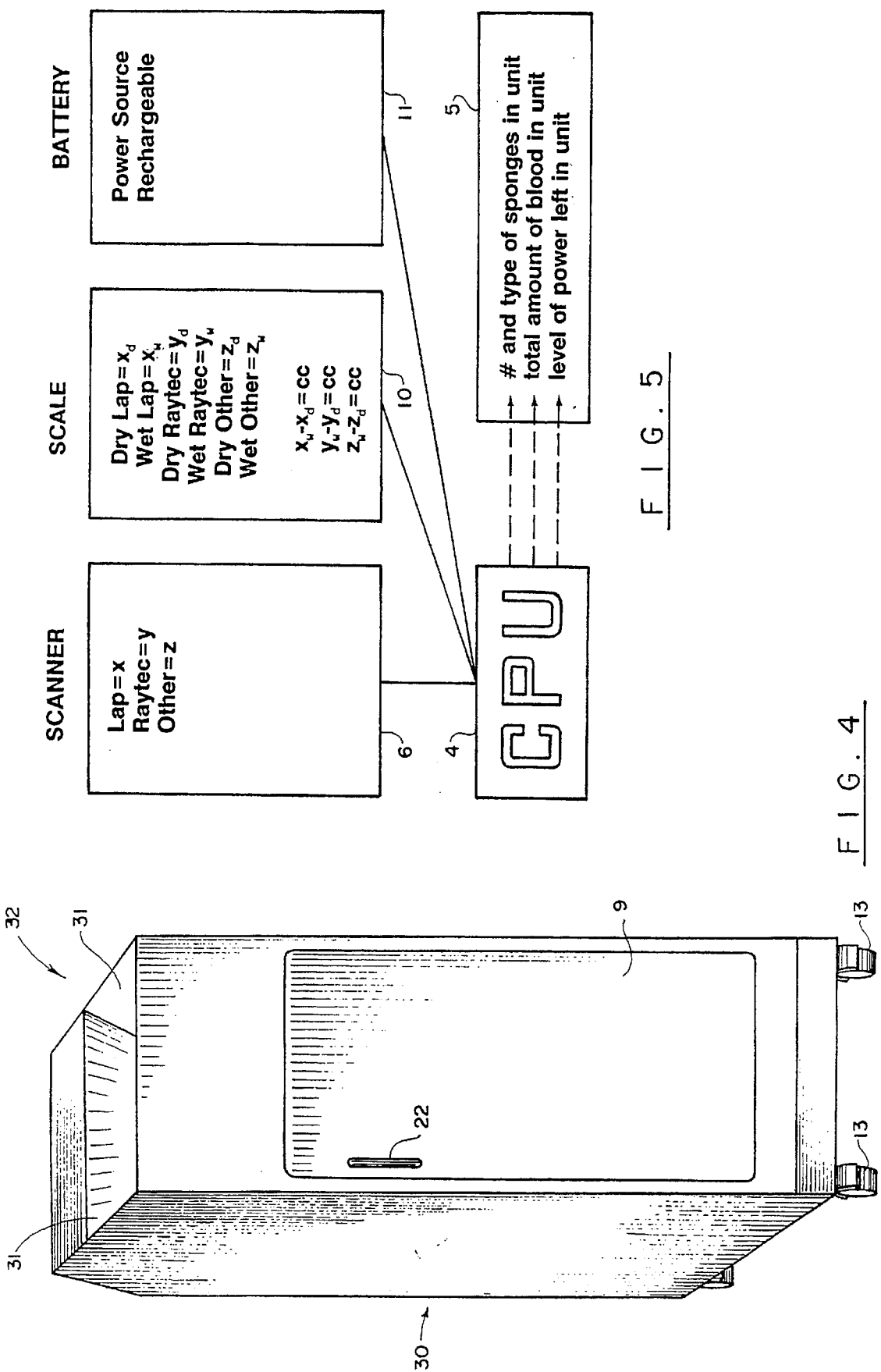

AUTOMATIC SURGICAL SPONGE COUNTER AND BLOOD LOSS DETERMINATION SYSTEM

Background of the Invention

1. Field of the Invention

The present invention relates to devices which collect, weigh and count surgical sponges.

2. General Background of the Invention

During surgery absorbent sponges are used to soak up blood and other body fluids in and around the incision site. Because the risk of a sponge being retained inside a patient is so great, surgical personnel go to great lengths to account for each and every sponge which is used in surgery. Strict sponge count policies have been developed by hospitals to deal with this issue. Moreover, surgeons and anesthesiologists determine blood loss by using visual inspection or the manual weighing of soiled sponges, thus soiled sponges are usually kept in one area of the operating room. Another area of concern regarding soiled surgical sponges is the risk of transmission of bloodborne diseases such as hepatitis B virus (HBV) and human immunodeficiency virus (HIV). To reduce exposure and contamination every precaution necessary should be taken to reduce risk of infection.

Sponge counts are an essential part of operating room procedure. They help ensure patient safety by reducing the chance that a sponge will be retained inside of the patient. Typical sponge count policies include: an initial count at the beginning of a procedure and subsequent counts throughout the procedure when additional sponges are added to the sterile field, before the closure of a deep incision, after the closure of a body cavity, when scrub or circulating personnel are relieved, and before the procedure is completed.

In addition, it is necessary for the anesthesiologist and surgeon to have an accurate measurement of blood loss contained in sponges, so that if excessive blood loss is occurring, blood components can be ordered and administered immediately. This information is provided by weighing soiled sponges and then subtracting the dry weight of the number of sponges weighed from the total.

Moreover, soiled sponges are a source of contamination, thus handling and exposure should be kept to a minimum. Procedures which reduce the transmission of bloodborne pathogens include making sure that soiled sponges are handled with gloves and instruments only and that used soiled sponges are appropriately contained and confined.

In 1992, the Occupational Safety and Health Administration (OSHA) issued new regulations regarding bloodborne pathogens in U.S. hospitals. Nearly 6 million healthcare workers in the United States who could be "reasonably anticipated" to come in contact with blood and other body fluids are subject to the new regulations. These regulations are intended to reduce worker exposure to hepatitis B virus (HBV), human immunodeficiency virus (HIV), or other bloodborne pathogens. Under the section on Engineering and Work Practice Controls, hospitals are required to eliminate or minimize employee exposure. This includes the implementation of new designs for devices which count sutures and sponges.

For more information about surgical sponge handling and counting, please see U.S. Pat. No. 4,422,548, incorporated herein by reference.

U.S. Pat. No. 3,367,431 discloses a device for automatically counting and weighing surgical sponges. However, the device cannot distinguish between different sponges. Also, the amount of blood contained in soiled sponges must be manually calculated. Further, it does not use removable disposable bags.

U.S. Pat. No. 4,295,537 discloses a sponge-collecting device that keeps count and determines the weight of blood-soaked sponges. However, the device cannot automatically distinguish between different sponges. Also, the device does not automatically count the sponges (the number and dry weight of the sponges must be manually input).

U.S. Pat. No. 4,422,548 discloses a sponge-collecting device that determines the weight of blood-soaked sponges. However, the device cannot automatically distinguish between different types of sponges. It also cannot determine the amount of blood in the sponges.

U.S. Pat. No. 5,009,275 discloses a sponge-collecting device that determines the weight of blood-soaked sponges. However, the device cannot automatically distinguish between different types of sponges, and so it cannot automatically determine the amount of blood loss when sponges of different dry weights are collected in the container.

SUMMARY OF THE INVENTION

The apparatus of the present invention solves the problems confronted in the art in a simple and straightforward manner. What is provided is a device which automatically counts surgical sponges and automatically determines the amount of blood contained in the sponges, without any input or calculations during the surgery by any person. The apparatus includes means for automatically determining the weight of the sponges when dry, and for deducting that weight from the total weight of the sponges and blood in the apparatus. The soiled sponges will be held inside of the device in a removable disposable bag. Means are also provided to keep a running total of the number of sponges which have entered the apparatus from a predetermined time, and the total amount of blood which has entered the device from a predetermined time, even when a full bag is removed and replaced with an empty bag in order to make room for additional sponges to enter the container.

The means for automatically determining the weight of the sponges when dry includes a non-optical scanner means which can read an indicating means on the sponges even when the indicating means is covered with blood or other body fluids.

The present invention comprises a system for facilitating counting of surgical sponges and determining the approximate amount of body fluids contained therein. It includes a plurality of sponges of varying weights, each sponge having a dry weight before being used to absorb fluids and an indicating means thereon for indicating the dry weight of the sponge, the dry weight of the sponge including the weight of the indicating means; and a device for counting the surgical sponges and determining the approximate amount of body fluids contained therein. The device comprises a container means for containing the surgical sponges, the container means having an opening above a receptacle means for receiving the surgical sponges, scanner means for detecting when one of the surgical sponges passes through the opening, and detecting means for automatically determining the dry weight of the surgical sponges which have passed through the opening since a predetermined time by detecting the indicating means on the sponges. The device also includes calculating means for automatically determining the approximate amount of body fluid contained in the surgical sponges which have entered the container since a predetermined time by subtracting the dry weight of the sponges from the weight of the sponges including the body fluids. The device further comprises first display means for displaying an indication of the approximate amount of body fluid contained in the surgical sponges which have entered the container since a predetermined time, determining means for automatically determining the number of surgical sponges which have entered the container since a predetermined time, and second display means for displaying the number of surgical sponges which have entered the container since a predetermined time.

The detecting means is capable of distinguishing between multiple types of surgical sponges, even those sponges of different types but similar weights, and the second display means displays the number of each type of sponge which is received.

The first display means indicates, with an accuracy of ±0.1%, the exact amount of body fluids contained in the sponges which have entered the container since a predetermined time.

The detecting means comprises a non-optical scanner means which can read an indicating means on the sponges even when the indicating means is covered with blood or other body fluids.

There are three main differences between the Baker device (that shown and described in U.S. Pat. No. 3,367,431) and the apparatus of the present invention. The device of the present invention is superior and different in the following areas: the ability to distinguish between different types of sponges and to give a visible running count of each type; the ability to automatically calculate the amount of blood contained in soiled sponges; and the provision of removable disposable bags to minimize handling of the soiled surgical sponges.

The ability to distinguish between different types of sponges and maintain a running count of each type is a major advantage of the present invention over the Baker device. The Baker device can only give a running count of total sponges used. It cannot break that number down by type. In the case of a miscount, knowing the breakdown of different size sponges helps narrow down where the mistake was made. Several Baker devices would have to be used to equal one device of the present invention.

The ability to identify what type of sponge has entered the device is essential to calculating the amount of blood contained in the soiled sponges. Pre-programmed dry weights for each type of sponge allows instant computation by the device of the present invention. The device of the present invention can instantaneously calculate blood loss and also store in memory this amount when the disposable bag is removed, thereby maintaining a constant readout throughout the procedure. Although the Baker device weighs soiled sponges, the calculation is still done manually. This calculation is extremely complicated and time-consuming given the different size sponges used. Each successive calculation gets more complicated due to the zeroing device which is utilized to help give a constant reading. An accurate measurement is dependent on how often the circulator calculates blood loss. Add to this, the findings of an article on blood loss determination in the Official Journal of the Association of Operating Room Nurses, (AORN) for June 1981, volume 33, No. 7 by Darden, which suggests that sponge tallies and weighing of sponges should be made at least every 15 minutes, otherwise determination of blood loss may be quite inaccurate due to evaporation. By instantly calculating blood loss and then holding this amount in memory, the present invention eliminates these inaccuracies. In addition, potential human error in the calculation is also eliminated.

The third difference between the two devices is the presence of a removable disposable bag in the device of the present invention. This feature will drastically reduce the handling of soiled sponges and thus the exposure of staff to blood. This is extremely important given the risk of infection to AIDS. When a sponge enters the device, it is deposited into a disposable bag where it will stay until the bag is removed and sealed. The Baker device requires personnel to remove the soiled sponges from the basket and then bag them for disposal.

It is an object of the present invention to provide a device which will automatically count surgical sponges, regardless of size, during surgery with a high degree of accuracy.

It is a further object of the present invention to provide, in a device of this type, in addition to means for giving a running count of sponges, means for simultaneously weighing sponges and instantly and accurately calculating the amount of blood contained in those sponges.

Another object of the present invention is to provide a device which collects soiled surgical sponges and facilitates their disposal with minimal handling.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 4 is a rear view of the preferred embodiment of the apparatus of the present invention;

FIG. 5 is a block diagram indicating the input and output of the CPU of the preferred embodiment of the apparatus of the present invention.

PARTS LIST

Figure 6:
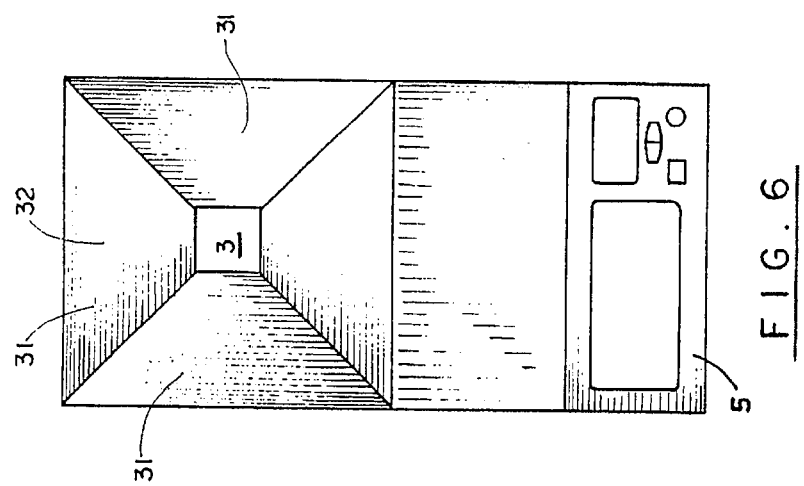
FIG. 6 is a top view of the preferred embodiment of the apparatus of the present invention.

The following is a list of suitable parts and materials for the various elements of the preferred embodiment of the present invention.

1 identification tag on sponge 2
2 sponge
3 opening in apparatus 30 for sponges 2
4 control unit (CPU)
5 display panel
6 reader
7 reader electronics
8 disposable bag
9 door
10 weighing scale
11 rechargeable battery
12 shelf for extra bags 8
13 wheels
14 retractable electrical cord
15 wiring interconnecting the reader electronics 7 and the reader 6

16 wiring interconnecting the reader electronics 7 and the control unit 4
17 wiring interconnecting the reader electronics 7 and the battery 11
18 wiring interconnecting the control unit 4 and the scale 10
19 wiring interconnecting the battery 11 and the scale 10
20 wiring interconnecting the battery 11 and the control unit 4
21 bag rack
22 handle for door 9
23 radio waves
30 automatic surgical sponge counter and blood loss determination apparatus
31 sloped sides of receptacle 32
32 receptacle
33 label
51 sponge type and quantity display screen
52 blood-loss display screen
53 battery charge indicator
54 on-off switch
55 alarm light

DETAILED DESCRIPTION OF THE PREFERRED EMBODIMENT

Figure 1:
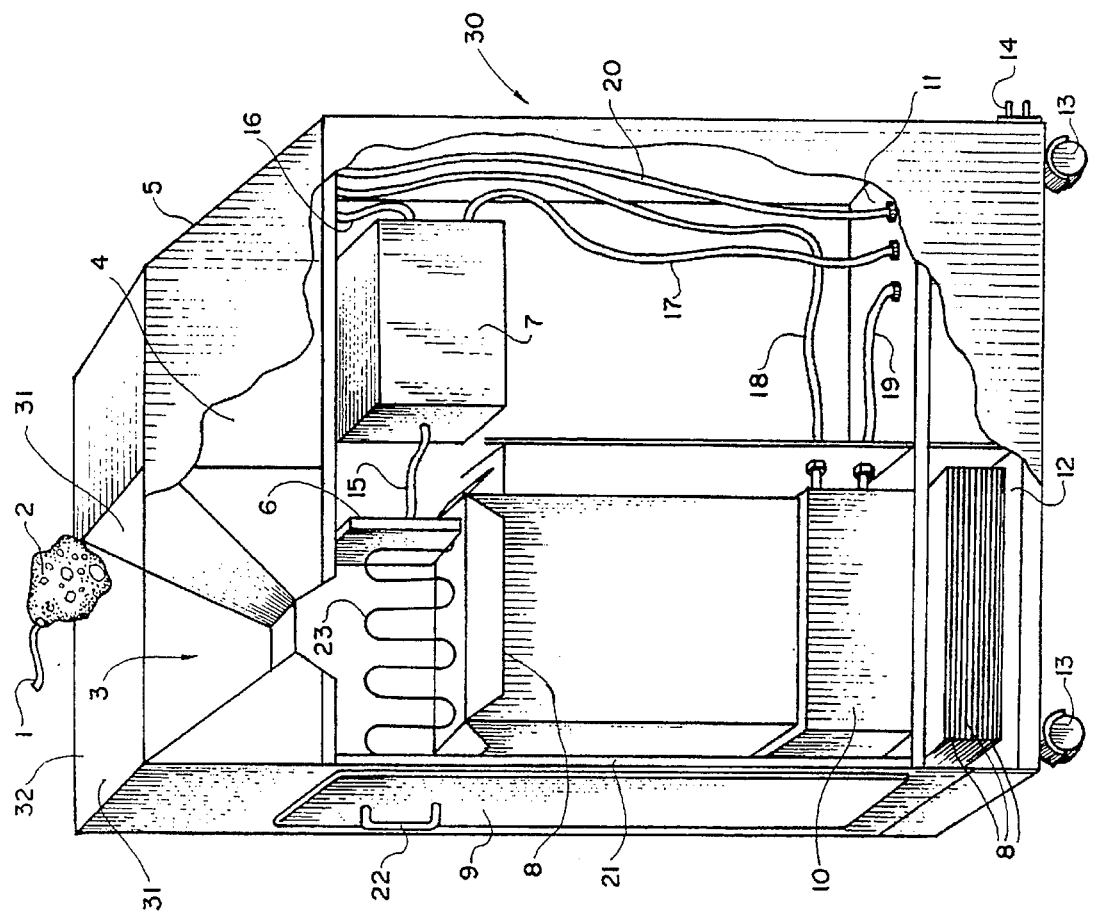
FIG. 1 is a cutaway, side view of the preferred embodiment of the apparatus of the present invention.
Figure 3:
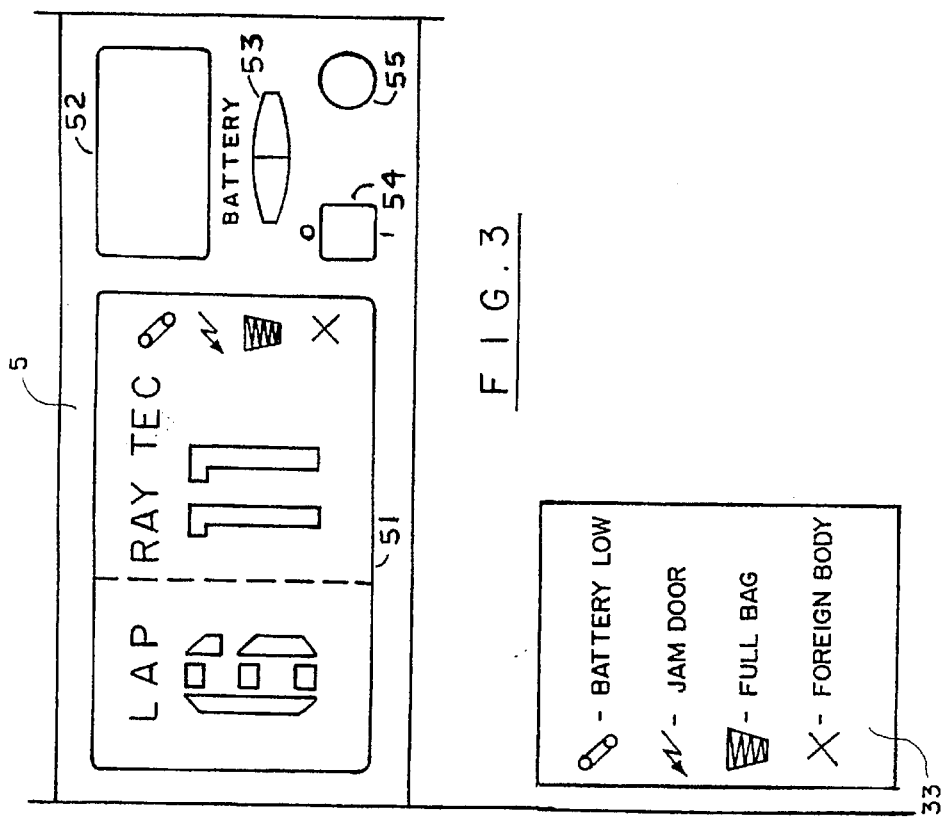
FIG. 3 is a detail of the control panel and display of the preferred embodiment of the apparatus of the present invention.
Figure 2:
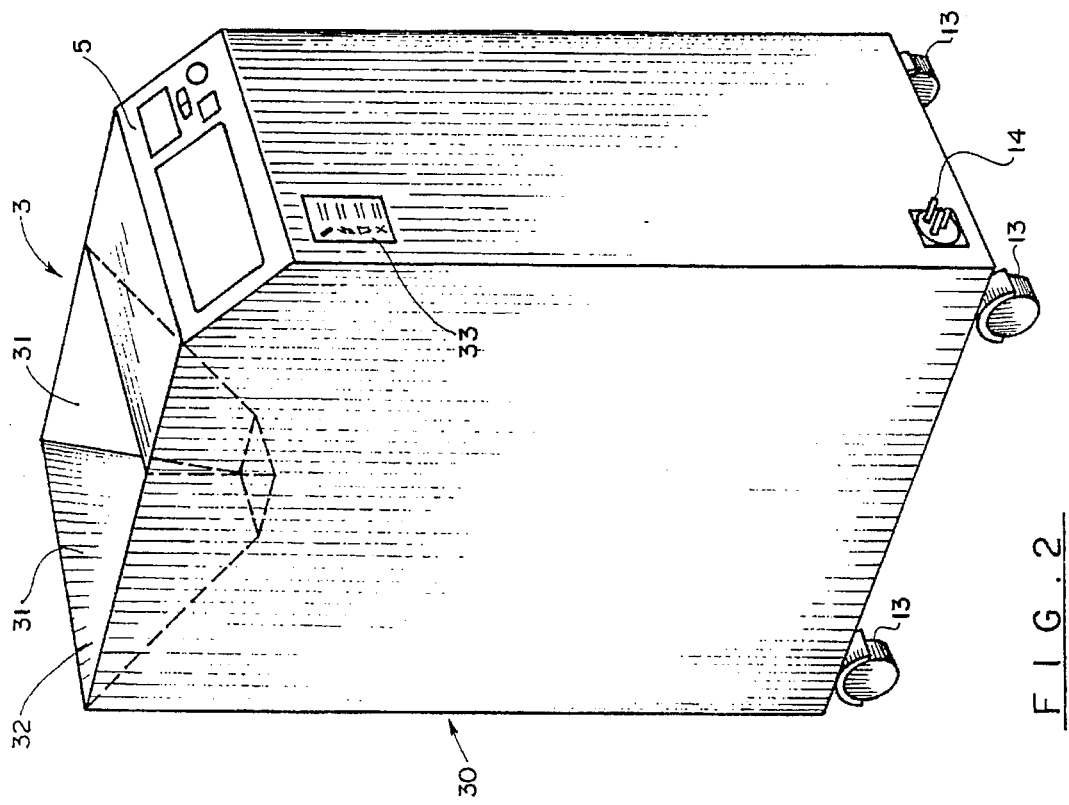
FIG. 2 is a perspective view of the preferred embodiment of the apparatus of the present invention.

The preferred embodiment of the present invention, automatic surgical sponge counter and blood loss determination apparatus 30, is shown in FIGS. 1 through 5.

The device (See FIG. 1) takes the place of a kickbucket which is now in use in operating rooms around the world. It is mobile (mounted on wheels 13, powered by rechargeable battery 11), compact in size (30"×18"×18", for example) and easy to operate. During an operation all surgical sponges 2 are deposited into the apparatus 30 by dropping them into a receptacle 32 having sloped sides 31 leading to an opening 3 at the top of apparatus 30. Receptacle 32 preferably has dimensions of 15" by 16", more preferably has dimensions of 16" by 18", and most preferably has dimensions of 1841 by 18". The top of The top of receptacle 32 is preferably about 20–40" above the floor, more preferably about 25–35" above the floor, and most preferably about 30" above the floor. Opening 3 preferably has dimensions of from 4" by 5 ½" to 6 ½" by 8 ½", and more preferably has dimensions of 5 ½" by 7".

To increase the chance that a sponge tossed at the apparatus of the present invention will land in receptacle 32, receptacle 32 is preferably rather large. To reduce evaporation from bag 8 and to make the scanner 6 relatively close to the sponges 2 passing through the opening 3, opening 3 is preferably relatively small. Preferably, the ratio of the size of opening 3 to the size of receptacle 32 is rather small.

As the sponge 2 passes through the opening, a reader 6 reads what type of a sponge has entered (Lap, Mini-Lap, Raytec, etc.) from a radio frequency tag 1 attached to the sponge 2. The control unit 4 receives data from the reader 6 along with data from the scale 10 and then processes this information using preprogrammed software. The final output is displayed on the display panel 5: a readout of the number of sponges contained in the unit, broken down by type, is displayed on screen 51; the amount of blood and other bodily fluids contained in the sponges is displayed (preferably in cubic centimeters) on screen 52. This amount will be calculated by the control unit 4 using a formula based on the weight of the sponges 2 soiled, minus the weight of the sponges 2 dry (different size sponges 2 have different dry weights; the dry weights of different sponges is preferably pre-programmed into the software so that nurses will no longer have to do this manually).

The battery charge is indicated on battery charge indicator 53, with the left side being red and lighting up if the charge is low, and with the right side being green and lighting up if the charge is sufficient. An on-off switch 54 lights up with a green light when the power is on.

Label 33 displays the symbols and explanations for a number of alarm conditions which cause alarm light 55 to light up. When one of the conditions displayed on label 33 occurs, the appropriate symbol flashes in screen 51. The conditions include a low battery charge condition, a jammed door, a full bag, and the presence of foreign objects (needles, hypos, cottonoids, bovie tips, etc.) inside of the device.

Once the sponge 2 passes the reader 6 it is deposited in a disposable bag 8 which is suspended from a rack 21 connected to a scale 10. The scale 10 weighs the contents of bag 8 and sends this data to the control unit 4 as mentioned above to be processed. Apparatus 30 can be programmed to alarm once a predetermined number of sponges 2 has been reached or when the bag 8 is full. The disposable bag 8 can then be removed through a rear door 9 and replaced with a new bag 8. A compartment 12 to store extra bags is provided. The memory of control unit 4 will continue to give a running count of sponges 2 as well as estimated blood loss amount for the duration of the entire surgical procedure. Once the operation is complete and all counts have been verified, the device 30 can be cleaned very easily, reset and ready for the next case. Because of the small size and mobility of apparatus 30, it can be moved from room to room effortlessly.

Tags 1 can preferably endure temperatures of up to about 400 degrees Fahrenheit (about 200 degrees Centigrade) to allow them to be autoclaved.

At the end of the day the device 30 can be plugged with plug 14 into an electrical outlet and recharged for the next day's use. Additional features can include: a gauge which indicates battery status by displaying the remaining life of the battery in hours and a low battery alert alarm. The battery 11 is rechargeable during operation of the device 30.

While other technologies may be available, radio frequency is believed to be the optimal technology. Radio frequency tags are preferred to other identifying means because they do not depend upon light for detection—they can be detected even when completely covered with blood. Other identifying means which can be attached to surgical sponges and which does not depend upon light for detection could be used.

Indala Corporation, San Jose, Calif. has a brochure dated 1993 (attached and hereby incorporated by reference) which discloses an RF technology, purportedly covered by U.S. Pat. No. 4,818,855 and Canadian Patent No. 1253591, which the inventors contemplate using with the present invention. These patents are also incorporated by reference. Specifically, the preferred tag to use with the present invention is the Indala IT-52 Mini Disc Tag. The IT-52 is a transfer-molded, chemical resistant plastic disk 7/16 "(11 mm) in diameter by 1/8 "(3 mm) thick. It has a weight of approximately one gram. The preferred reader 6 for the apparatus of the present invention is the Indala IR-50; the IR-50 can read the IT-52 at a range of 4 "(100 mm). The tag 1 is preferably attached to a surgical sponge by being sewn onto the sponge with and where the radio opaque marker is currently attached. The information which tag 1 contains is preferably simply a number—in the control unit 4, that number is associated with information (such as brand name, dry weight, and size) about the sponge 2 to which tag 1 is attached. Control unit 4 is pre-programmed with information about each different type of sponge which is used with apparatus 30. This sort of system may be more economical than one in which all information about the sponge is contained in the tag 1, and may make it easier to convert from one tag technology to another.

Advantages of the Device of the Present Invention

The sponge count is an essential part of operating room procedure. It not only assures patient safety, but it also provides the medical team with an ongoing estimation of blood loss. Current methods for handling surgical sponges are antiquated and inadequate in today's modern and potentially dangerous operating room environment. Even in the newest hospitals, sponges are still counted and weighed manually. These procedures are time-consuming, prone to human error and unnecessarily expose medical staff to blood contact. The present invention addresses these shortcomings by integrating all sponge-related functions into one fully automated unit. The present invention is different from prior art on the subject of sponge management in that it has the ability to distinguish between different types of sponges, maintain a running count of each type of sponge being used in a given procedure, and automatically calculate the amount of blood contained in those sponges, instantly. These improvements will dramatically affect sponge management in the areas of safety, sponge counts and blood measurement.

Safety: The present invention will have its biggest impact in the area of increased safety for medical staff. Exposure to bloodborne pathogens will be significantly reduced due to less handling of soiled sponges and the closed environment of the device. Currently, soiled sponges are handled several times by different members of the medical team. They are first handled by scrub personnel. Next they are counted by the circulating nurse. They are then bagged, weighed when necessary, and if a count is incorrect, they are removed from the bags and recounted. Finally, an orderly has to clean the area where the sponges are handled. With the present invention, soiled sponges will only be handled once by the staff member who deposits the sponge into the device. The device will then do the counting, estimate blood loss amount and store the sponges in a disposable bag. This will be done in a closed environment as opposed to an open bucket thereby reducing airborne contamination and also reducing the time spent cleaning areas where sponges are counted. Because the disposable bag is enclosed inside of the device, less bloodborne pathogens can escape due to evaporation.

Sponge Counts: The present invention will increase the accuracy of sponge counts by eliminating human error and providing a running count of sponges already used. It will give a visible readout of all different types of sponges used during a given procedure. This is important because it allows the staff to constantly check counts throughout the procedure. An increase in accuracy reduces the chances that a sponge will be left in a patient. This increases safety for the patient and reduces the time that is spent recounting sponges, thus reducing total count time. Also, because the device contains a disposable bag, staff will no longer have to bag sponges manually, thus saving time. The technology that is preferred to be used to do the scanning (radio frequency) is extremely accurate (fewer than 1 error out of 1,000,000).

Estimated Blood Loss Measurement: The present invention has the ability to weigh soiled sponges, automatically compute blood loss, and give a constant visible readout of that amount. This is an important feature for several reasons. A constant readout is valuable to anesthesiologists and surgeons who use this information as one component in estimating total blood loss for a given procedure. Instant information is helpful when ordering blood components and reduces guessing on blood loss amount. In the case of small children or infants this information is critical. Currently, surgeons and anesthesiologists have to estimate the amount of blood loss by sight and the manual weighing of sponges, which is done by the circulating nurse. Besides the time saved in weighing and doing a manual calculation of blood loss, the device reduces human error in the calculation. This increases safety for the patient. Also, a reduction in time spent handling soiled sponges reduces staff exposure to blood.

The apparatus of the present invention counts surgical sponges (Laps, Raytecs, etc.) with a high degree of accuracy. It constantly calculates the amount of blood and other bodily fluids in the sponges. It includes a rechargeable battery 11 and can include a visible battery gauge which displays the remaining life of the battery in hours. It has an alarm which goes off when the charge in the battery 11 drops below a predetermined amount. The battery 11 is rechargeable during operation of device 30.

The container 30 of the present invention is compact in size, and can have exemplary dimensions of one foot by two feet, which is bigger than a standard a kick bucket.

Container 30 is mobile and durable. It can distinguish between different types of sponges (Laps, Raytec, Mini-Laps, etc.). It includes disposable bags. It is simple and easy to operate, and has the operating instructions on its face. Disposable bags 8 have a capacity of at least forty sponges when properly installed upon rack 21 of device 30.

Container 30 can interrupt the count and maintain the sponge count and blood loss amount. An alarm sounds when it is time to change bag 8 (that is, when a predetermined number of sponges have entered container 30 since the last change of the bag). An alarm could also sound when a foreign object is present in the container 30.

The device 30 of the present invention can read tags 1 even when the tag 1 is hidden or covered with blood. Device 30 is easily and quickly cleaned. It is water-resistant and does not have to be sterile.

The reader 6 can preferably detect up to six tags 1 at one time. It preferably can detect foreign objects, such as needles, hypodermic needles, cottonoids, bovie tips, etc. The count can be interrupted to allow the inspection of foreign matter.

The ability to distinguish between different types of sponges helps to accurately estimate the amount of blood lost during surgery. For example, Raytec sponges weigh, when dry, about five grams. Lap sponges weigh, when dry, about 20 grams. When soaked with blood and/or other bodily fluids, Raytec sponges can weigh up to about 50 grams and Lap sponges can weigh up to about 120 grams. Suppose, for example, that forty sponges are used during an operation, and half are Raytec sponges and the other half are Lap sponges. The total weight of blood and sponges is about 1,500 grams, with 500 grams representing the dry weight of the sponges and 1,000 grams representing the weight of the blood and other bodily fluids (1,000 cc's of fluid). If all of the sponges were treated as being Lap sponges, then the calculation would improperly treat 300 grams of blood as dry weight of the sponges. Thus, the amount of estimated fluid lost would be improperly reduced by 300 grams (300 cc's of blood). The weight of tags 1 is not being considered, since tags 1 weigh the same whether attached to a Raytec sponge or to a Mini-lap sponge.

The following are advantages that key personnel and hospitals who utilize the present invention will realize.

For nurses, the invention: reduces count time; reduces exposure to blood; reduces risk of infectious disease;

increases accuracy of count; increases patient contact; increases attentiveness to procedure; increases attentiveness to surgeon's needs; increases attentiveness to anesthesiologist's needs; increases attentiveness to surgical tech's needs; and increases productivity by freeing the nurse for other duties.

The surgeons and anesthesiologists benefit because the present invention: increases accuracy of blood loss amount; increases response time on checking and ordering blood components; and reduces guessing on blood loss amount.

The hospital benefits from the present invention because: it helps to provide a safer environment for operating room employees due to less exposure to bloody sponges; it increases accuracy of sponge counts; it causes a reduction in repeat surgeries to extract sponges left in wounds; it causes a reduction in costs and risks associated with repeat surgeries; it causes an increase in productivity of the Circulating Nurse; it causes an increase in quality of patient care due to more attentive O.R. Nurse, less chance of repeat surgery due to sponge left in wound, and reduced guessing on blood loss by anesthesiologists.

While it is preferred to use radio frequency tags and an associated detector, other means for distinguishing one type of sponge from another could be used, such as an electric eye, metal indicators, color indicators.

The foregoing embodiments are presented by way of example only; the scope of the present invention is to be limited only by the following claims.

We claim:

1. Apparatus for automatically counting used surgical sponges and determining the amount of blood contained in the surgical sponges, each sponge having a dry weight before being used to absorb fluids and an indicating means thereon for indicating the approximate dry weight of the sponge, the approximate dry weight of the sponge including the weight of the indicating means, the apparatus comprising:
   (a) a container for containing used surgical sponges, the container having an opening through which used surgical sponges enter the container;
   (b) detecting means, comprising a non-optical scanner means, for detecting a surgical sponge entering the container through the opening;
   (c) first display means for displaying the number of sponges which have entered the container through the opening since a predetermined time;
   (d) determining means for automatically determining the approximate dry weight of a sponge entering the container through the opening by detecting the indicating means on the sponge;
   (e) weighing means for weighing the contents of the container;
   (f) calculating means for automatically calculating the approximate amount of body fluids which has entered the container through the opening since a predetermined time; and
   (g) second display means for indicating the approximate amount of body fluids contained in all sponges which have entered the container means through the opening since a predetermined time.

2. The apparatus of claim 1, wherein:
the non-optical scanner means can read an indicating means on the sponges even when the indicating means is covered with blood or other body fluids.

3. The apparatus of claim 1, further comprising:
disposable bag means for receiving sponges which enter the container through the opening;
access means for allowing access to the disposable bag means to allow removal of the disposable bag means.

4. The apparatus of claim 1, further comprising:
first alarm means for indicating when a predetermined number of sponges is contained in the container.

5. The apparatus of claim 1, wherein:
the apparatus further comprises means for automatically determining the type of sponge which enters the container means; and
the first display means includes means for indicating the number of each different type of sponge which has entered the container means through the opening since the predetermined time.

6. The apparatus of claim 1, further comprising:
a battery for powering electronic components in the container;
a visible battery gauge;
an alarm means for indicating when the battery power is low; and
an indication of remaining battery life.

7. The system of claim 1, wherein:
the second display means indicates, with an accuracy of ±0.1%, the exact amount of body fluids contained in the sponges which have entered the container since the predetermined time.

8. The apparatus of claim 1, further comprising:
memory means containing the weight of various sponges to be used with the apparatus.

9. A system for facilitating counting of surgical sponges and determining the approximate amount of body fluids contained therein, comprising:
   (a) a plurality of sponges of varying weights, each sponge having a dry weight before being used to absorb fluids and an indicating means thereon for indicating the dry weight of the sponge, the dry weight of the sponge including the weight of the indicating means;
   (b) a device for counting the surgical sponges and determining the approximate amount of body fluids contained therein, comprising:
      (b1) a container means for containing the surgical sponges,
      (b2) an opening in the container means above a receptacle means for receiving the surgical sponges;
      (b3) scanner means for detecting when one of the surgical sponges passes through the opening;
      (b4) detecting means for automatically determining the dry weight of the surgical sponges which have passed through the opening since a predetermined time by detecting the indicating means on the sponges;
      (b5) calculating means for automatically determining the approximate amount of body fluid contained in the surgical sponges which have entered the container since a predetermined time by subtracting the dry weight of the sponges from the weight of the sponges including the body fluids;
      (b6) first display means for displaying an indication of the approximate amount of body fluid contained in the surgical sponges which have entered the container since a predetermined time;
      (b7) determining means for automatically determining the number of surgical sponges which have entered the container since a predetermined time; and
      (b8) second display means for displaying the number of surgical sponges which have entered the container since a predetermined time.

10. The system of claim 9, wherein:

different types of surgical sponges are received by the container, and the detecting means is capable of distinguishing between multiple types of surgical sponges, even those sponges of different types but similar weights, the second display means displays the number of each type of sponge which is received.

11. The system of claim 9, wherein:

the first display means indicates, with an accuracy of ±0.1%, the exact amount of body fluids contained in the sponges which have entered the container since a predetermined time.

12. The system of claim 9, wherein:

the detecting means comprises a non-optical scanner means.

13. The system of claim 13, wherein:

the non-optical scanner means can read an indicating means on the sponges even when the indicating means is covered with blood or other body fluids.

* * * * *